United States Patent
Neubauer et al.

(10) Patent No.: US 6,551,325 B2
(45) Date of Patent: Apr. 22, 2003

(54) DEVICE, SYSTEM AND METHOD FOR DETERMINING THE POSITION OF AN INCISION BLOCK

(75) Inventors: Timo Neubauer, München (DE); Martin Immerz, München (DE)

(73) Assignee: BrainLAB AG, Kirchheim/Heimstetten (DE)

(*) Notice: Subject to any disclaimer, the term of this patent is extended or adjusted under 35 U.S.C. 154(b) by 0 days.

(21) Appl. No.: 09/860,026

(22) Filed: May 17, 2001

(65) Prior Publication Data

US 2002/0068942 A1 Jun. 6, 2002

(30) Foreign Application Priority Data

Sep. 26, 2000 (EP) .......................... 00 120 229
Feb. 6, 2001 (EP) .......................... 01 102 714

(51) Int. Cl.[7] ................................................ A61F 2/38
(52) U.S. Cl. .............................. 606/88; 606/87; 606/90
(58) Field of Search .............................. 600/86, 87, 98, 600/97, 96, 90, 88, 426; 74/490.07, 490.03; 248/124.1; 623/16.11

(56) References Cited

U.S. PATENT DOCUMENTS

| | | | | |
|---|---|---|---|---|
| 5,417,694 A | * | 5/1995 | Marik et al. .................. 606/88 |
| 5,624,444 A | * | 4/1997 | Wixon et al. ................. 606/88 |
| 5,788,700 A | * | 8/1998 | Morawa et al. ............... 606/88 |
| 5,911,723 A | * | 6/1999 | Ashby et al. ................. 606/88 |
| 6,077,270 A | * | 6/2000 | Katz .......................... 606/102 |
| 6,096,043 A | * | 8/2000 | Techiera et al. .............. 606/87 |
| 6,226,548 B1 | * | 5/2001 | Foley et al. ................. 600/426 |

FOREIGN PATENT DOCUMENTS

| WO | 97/23172 | 7/1997 |
|---|---|---|
| WO | 99/15097 | 4/1999 |
| WO | 99/60939 A | 12/1999 |

OTHER PUBLICATIONS

Thomas C. Kienzle III et al., "Total Knee Replacement", IEEE Engineering in Medicine and Biology Magazine, US, IEEE Inc. New York, No. 3, pp. 301–306, May/Jun. 1995.

* cited by examiner

Primary Examiner—Pedro Philogene
(74) Attorney, Agent, or Firm—Renner, Otto, Boisselle & Sklar, LLP

(57) ABSTRACT

The invention relates to a device (20, 30) for determining the position of an incision block (1, 10) comprising: a positioning element (21, 31) with at least one reference point (22a, 22b, 22c; 33a, 33b, 33c), whose spatial position can be detected; and a position determining element (24a, 24b; 34) which is firmly connected to the positioning element (21, 31), as well as to a method for determining the position of an incision block, wherein: the location of a positioning element (41) on a body structure, in particular on a bone, is detected; the location of a positioning element (21, 31) for positioning a position determining element (24a, 24b; 34) is detected; and the relative location of an incision block (1, 10) to the body structure is determined from the location of the positioning element (41) and the location of the positioning element (21, 31).

16 Claims, 8 Drawing Sheets

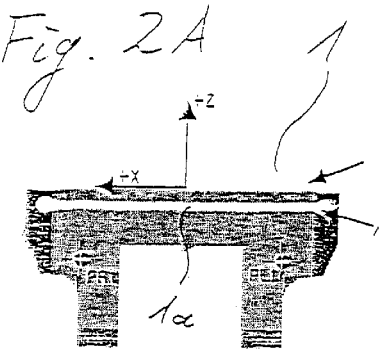
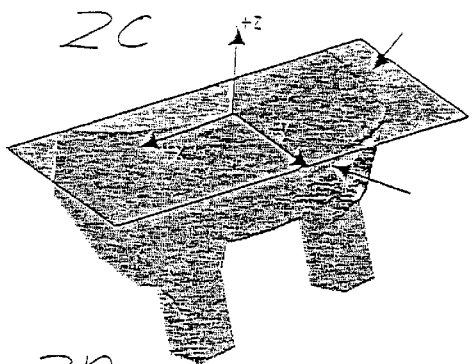
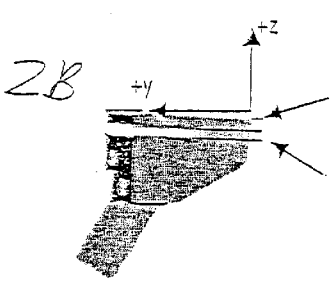
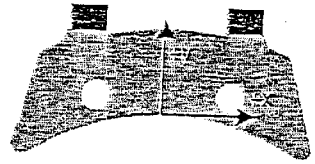
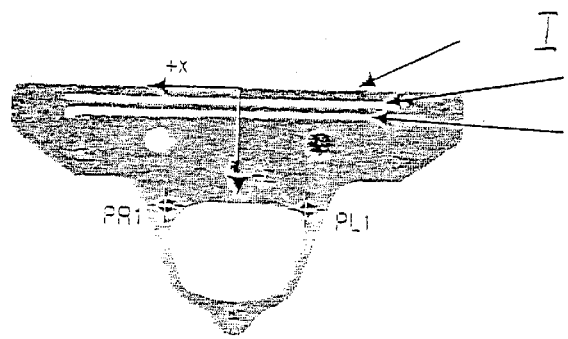
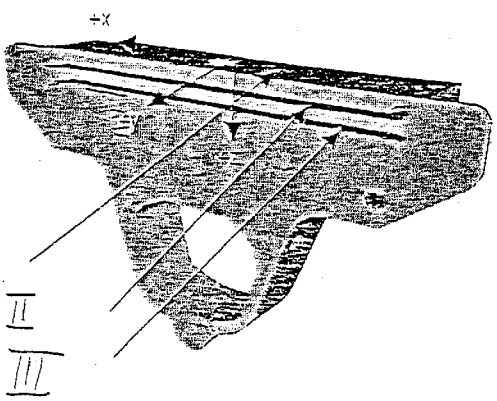

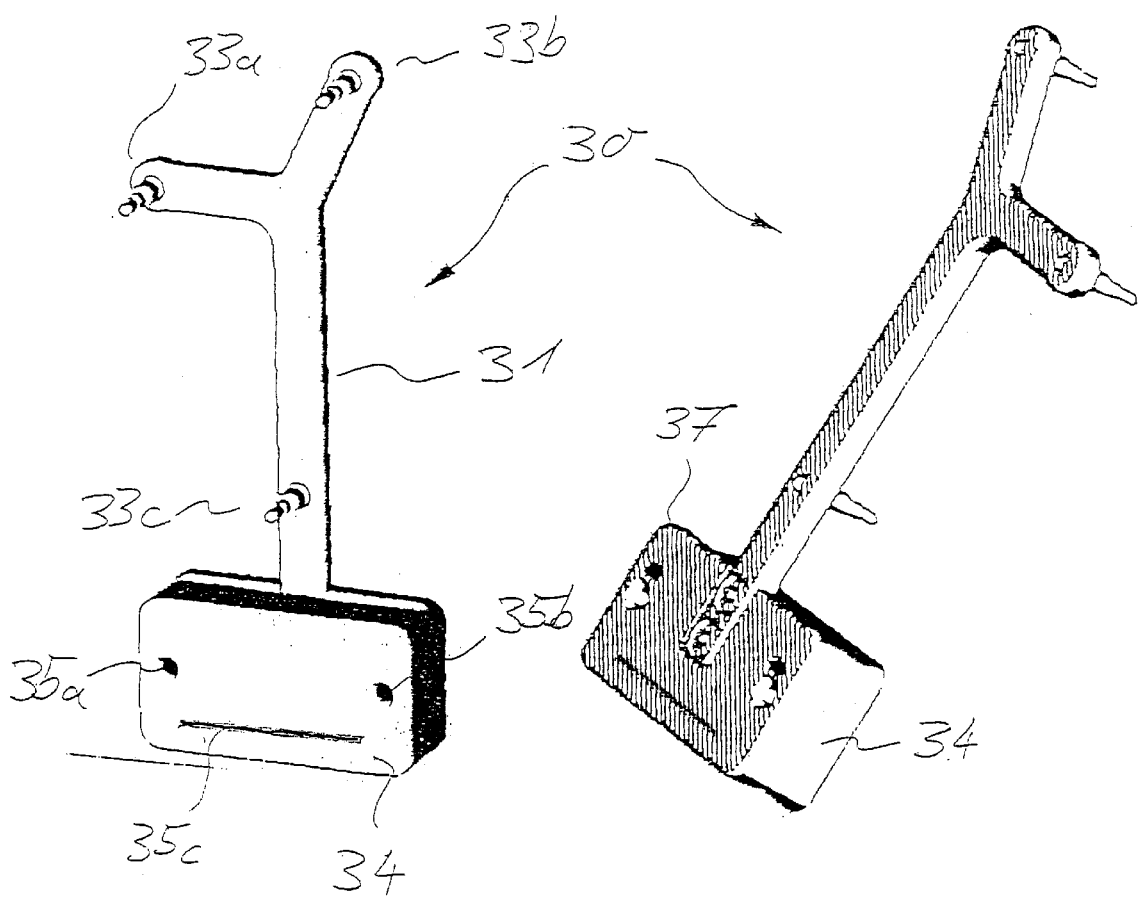

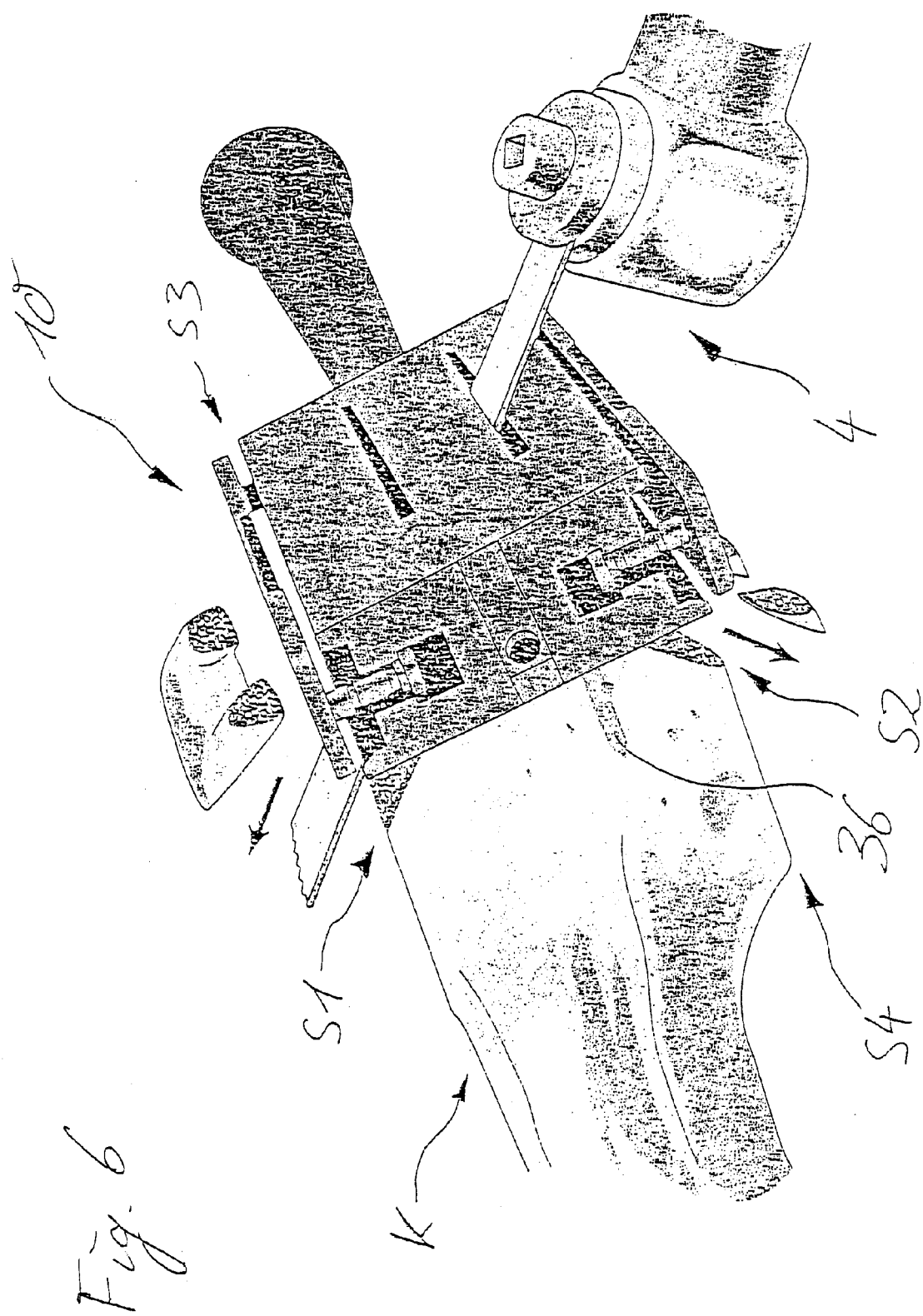

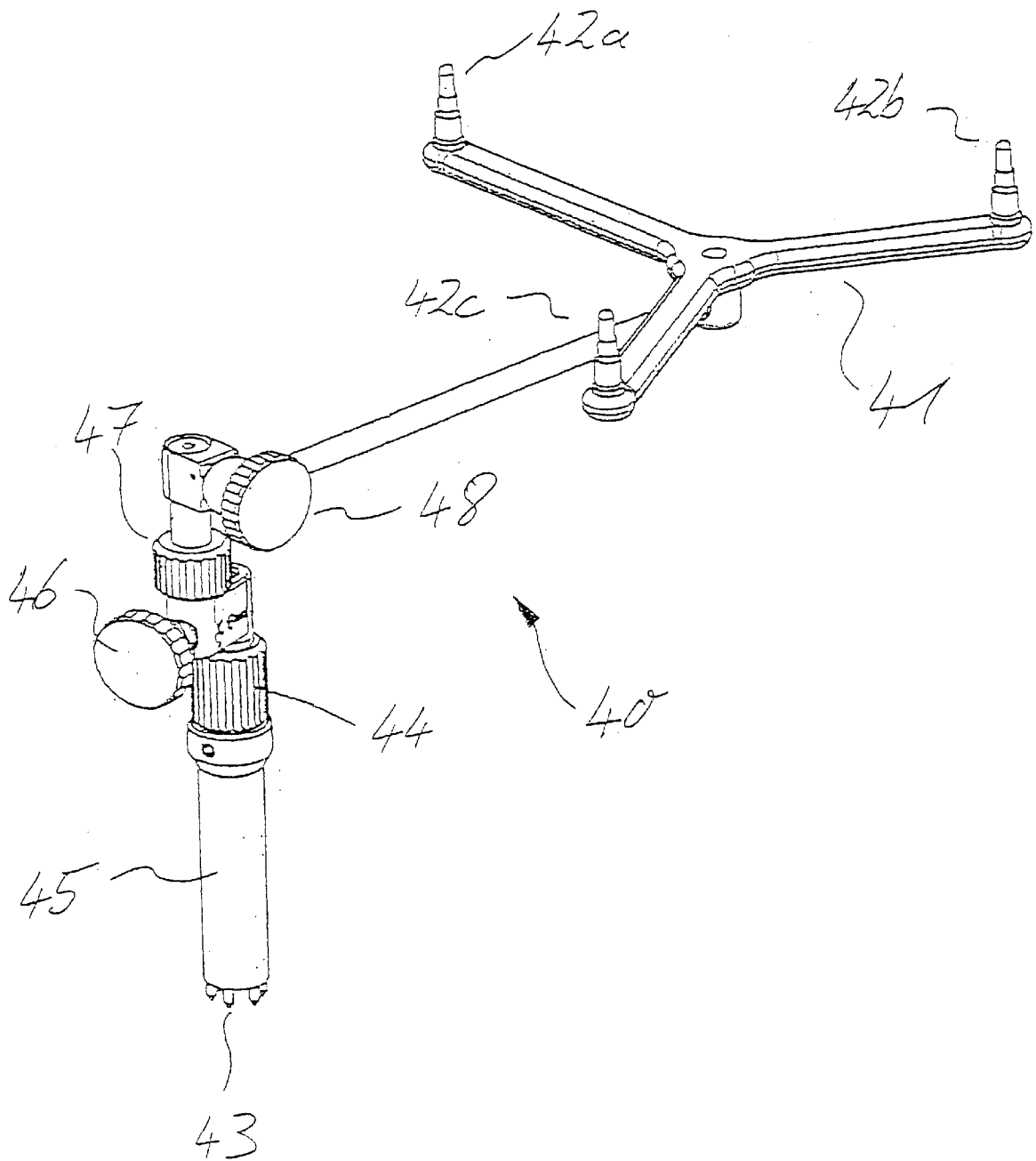

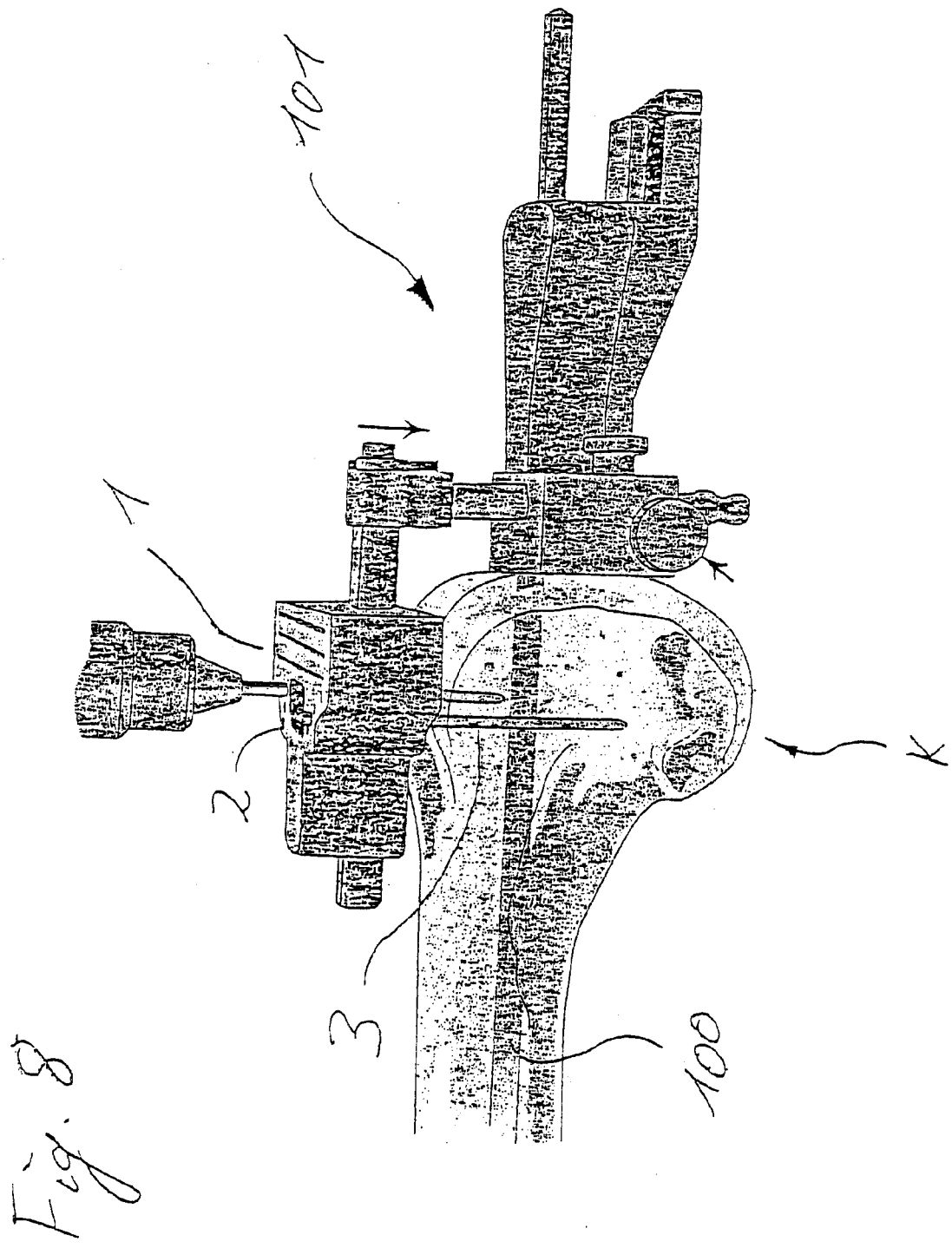

DEVICE, SYSTEM AND METHOD FOR DETERMINING THE POSITION OF AN INCISION BLOCK

FIELD OF THE INVENTION

The present invention relates to a device, system and method for determining the position, in particular for example the spatial position or the position relative to a system of co-ordinates, or for positioning or preparing the positioning of a medical operating instrument, an incision block or a bone or part of a bone.

BACKGROUND OF THE INVENTION

When attaching implants, such as artificial knee, elbow, finger or hip joints, it is required that the implant, such as a joint or part of a bone, is positioned as accurately as possible onto the adjacent bone. For this, the most accurate possible incisions must be made to the bone structures adjacent to the joint. FIG. 8 shows in diagram form the positioning of an incision block 1 onto a femoral bone, in accordance with the prior art. For this purpose, a guide rod 100 is inserted into a bone K, a positioning mechanism 101 being provided at the external end of the guide rod 100 for positioning and holding the incision block 1 in a desired position. Once the incision block 1 has been placed in the desired position, then positioning pins 3, for example screws, nails or pins, may be inserted into the bone K through holes 2 provided in the incision block, to fix the incision block 1. Once the incision block 1 has been fixed onto the bone K, a first incision plane S0 can be made, preferably as vertically as possible or at a slight angle to the mechanical axis of the bone, by means of a cutting tool 4, as shown in diagram form in the FIGS. 4A and 4B. In the example of the femoral bone, additional incisions must be made in additional planes S1 to S4, running obliquely or at an angle to incision plane S0 as shown in FIG. 6, in order to be able to position the corresponding knee implant component onto the bone. For this purpose, a second incision block 10 is placed on the first incision plane S0 and positioned by means of a suitable mechanism, further lateral incisions being made to the bone K with said second incision block 10, by guiding the cutting tool 4 into the obliquely running or lateral slits of the second incision block 10.

SUMMARY OF THE INVENTION

It is the object of the present invention to propose a device, a system and a method for determining the position of an incision block or a medical operating instrument or a bone or part of a bone, whereby this determining of position is simplified.

This object is solved by the features of the independent claims. Advantageous embodiments arise from the subclaims.

The device in accordance with the invention for determining the position of an incision block, in particular for a surgical method such as for example the creation of one or more incision surfaces for an artificial joint, comprises a positioning element with at least one reference point, whose spatial position can be detected. The positioning element can be either active and/or passive elements which output and/or reflect suitable signals which are detected by corresponding recording devices, such as for example cameras, in order to be able to determine the spatial location of the positioning element and the device connected to it. Furthermore, the device in accordance with the invention is provided with a position determining element, allowing the position of an incision block on a bone to be determined directly or indirectly.

If the spatial location of the bone or of another body structure is known, then the relative location to the bone, for example, can be determined, and a device placed in a desired position on the bone, based on this information. This procedure is generally referred to as "navigating".

In a first embodiment of the invention, a connecting element is provided on the device in accordance with the invention as a position determining element, which may be placed in a defined positional relationship to the incision block to be positioned, and connected with and/or attached to it. This may be one or more plate-shaped elements, for example, wherein at least one of these plate-shaped elements can be inserted, for example, into the guide slit of an incision block, in order to place and/or navigate the incision block into the desired position on the bone, in which an incision can be made in the desired plane by guiding a suitable cutting tool through the guide slit located in the incision block, preferably after fixing the incision block on the bone and removing the device in accordance with the invention. In general, however, other connections between the device in accordance with the invention and the incision block are also possible, as long as a desired, defined positional relationship between the device in accordance with the invention and the incision block is maintained, and as long as it is possible to navigate the cutting plane defined by the guide protection to the desired point.

If plates, or pegs lying in a plane, are used which can be inserted into a guide slit of the incision block, it is advantageous to provide a number of plates or pegs which preferably lie in a plane and have different thicknesses or diameters, in order to be able to insert these plates or pegs into guide slits of differing widths into the incision block.

In general, if the positional relationship between positioning element and connecting element is known, the connecting element can be arranged on the device in accordance with the invention, for example shiftably, or rotatably about an axis. If, for example, plates are used for insertion into the guide slits of an incision block, then the incision block can be exactly positioned in the desired plane, even if the plates are rotated or shifted, since the rotation of a plate about an axis parallel to the vertical of the plate surface can also be interpreted as shifting in a plane, and since the incision block is to be positioned accurately with reference only to the desired incision plane which in theory can extend infinitely. A shift of the incision block which does not alter the incision plane defined by the guide slit in the incision block is therefore insignificant.

In accordance with the first embodiment, an incision block can therefore be positioned by correctly aligning the desired incision plane, i.e. by navigating the incision plane and/or the guide slit of the incision block. This way of positioning an incision block is preferably used for positioning the first incision block as shown in FIGS. 4A and 4B, for cutting a plane preferably perpendicular or at a slight angle to the mechanical axis of the bone.

In accordance with a second embodiment of the invention, which may be used in combination with the first embodiment or separately as an independent, individual embodiment, a device for preparing and/or creating a connecting structure between the bone and the incision block may be used as the position determining element.

This device for preparing or creating a connecting structure can for example be a hole template and/or a fissure template with at least one through hole or fissure defined by the template, which is placed in the desired position, for example on a bone, using the positioning element connected to the template. Guide holes are provided in the hole template, which may be used for drilling holes in the bones or for inserting suitable connecting elements into the bones, for example pins, nails or screws. Guide fissures are provided in a fissure template, which may be used for sawing or fraising slots or fissures in the bones or for inserting suitable connecting elements into the bones, for example plates. A combination of hole temple and fissure template is also possible. A second incision block, such as for example the second incision block illustrated in FIG. 6, can be attached to or slipped onto on these connecting structures prepared with the aid of the template and/or these aligned connecting elements, such as for example holes drilled with the hole template. The position of the second incision block is thus determined only indirectly through the template, for example the hole template, as opposed to the first embodiment. In general, however, the first or the second incision block can be directly or indirectly positioned.

In this way, the template can be shifted, for example, on the first plane S0 created with the aid of the first incision block, and need only be shifted into a desired position on said plane S0, complete navigation in three-dimensional space not being required. However, such three-dimensional navigation of the template to the desired place may also be carried out.

Fixing elements on the bearing surface of the template, for example spikes, may serve to fix the template on the already created plane S0, which can be pressed into the soft structure of the bone tissue by applying a gentle pressure on the opposite side of the template.

A reference star with three passive markers arranged on it is preferably provided as the positioning element, preferably comprising a first geometry for navigating the first embodiment by inserting a small plate into a guide slit of the incision template, this geometry preferably being different to the geometry and/or arrangement for navigating the hole template of the second embodiment. In this way, the reference stars can be clearly assigned to the elements navigated by these reference stars respectively.

The system in accordance with the invention for determining the position of an incision block consists of the device above described and the incision block itself, as described in the first embodiment, or of the device above described and a device for preparing and/or creating a connecting structure, such as for example the hole template described in the second embodiment.

Suitable positioning elements, such as for example a reference star, are also preferably provided on the body structure to be treated, for example on a bone which is to be incised, in order to be able to exactly navigate these devices from the spatial positional information acquired in this way, in combination with the positional information of the guided incision block or of the hole template.

In the method in accordance with the invention for determining the position of or for navigating an incision block, the position of the positioning elements attached to a body structure, for example to a bone, is firstly determined, from which the spatial position of, for example, the bone or a joint may be determined. Moreover, the spatial position of the positioning elements of an incision block or of a hole template is determined, such that the relative positional relationship between the body structure, for example the bone, and the incision block or hole template can be determined from these two items of positional information. Based on this relative position, the incision block or hole template may be navigated to a desired place. For this, suitable display devices can be provided which show the relative positional relationship.

DESCRIPTION OF THE FIGURES

The invention will now be described by way of preferred embodiments. There is shown:

FIGS. 2A to 2D various views of a tibial incision block;

FIG. 3 two views of a femoral incision block;

FIGS. 5A and 5B a navigable slit template and hole template in accordance with the second embodiment;

FIG. 6 incision of further incision planes S1 to S4 using a second incision block positioned in accordance with the second embodiment;

FIGS. 7A and 7B two embodiments of a clamping device in accordance with the invention, suitable for attaching a reference star to a bone;

FIG. 8 positioning an incision block according to the prior art.

DETAILED DESCRIPTION OF THE INVENTION

Figure 1:
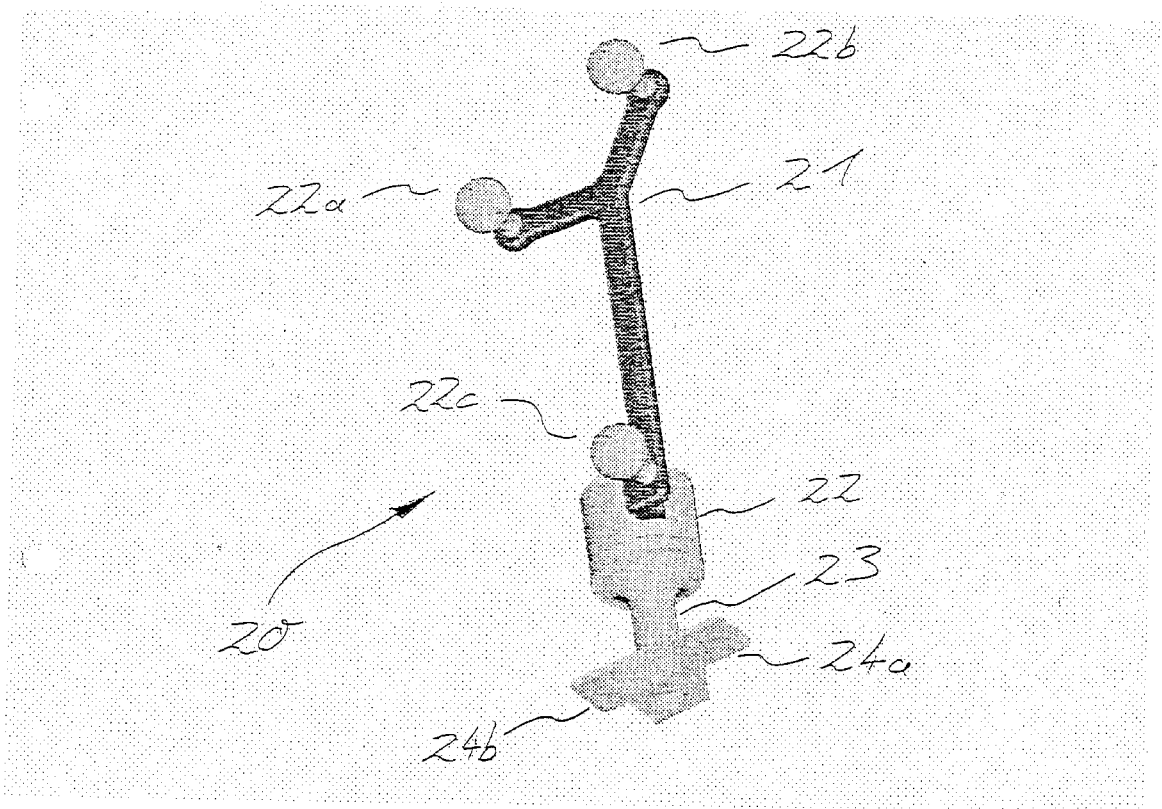
FIG. 1 a device in accordance with the invention for positioning an incision block in accordance with the first embodiment.
Figure 4A:
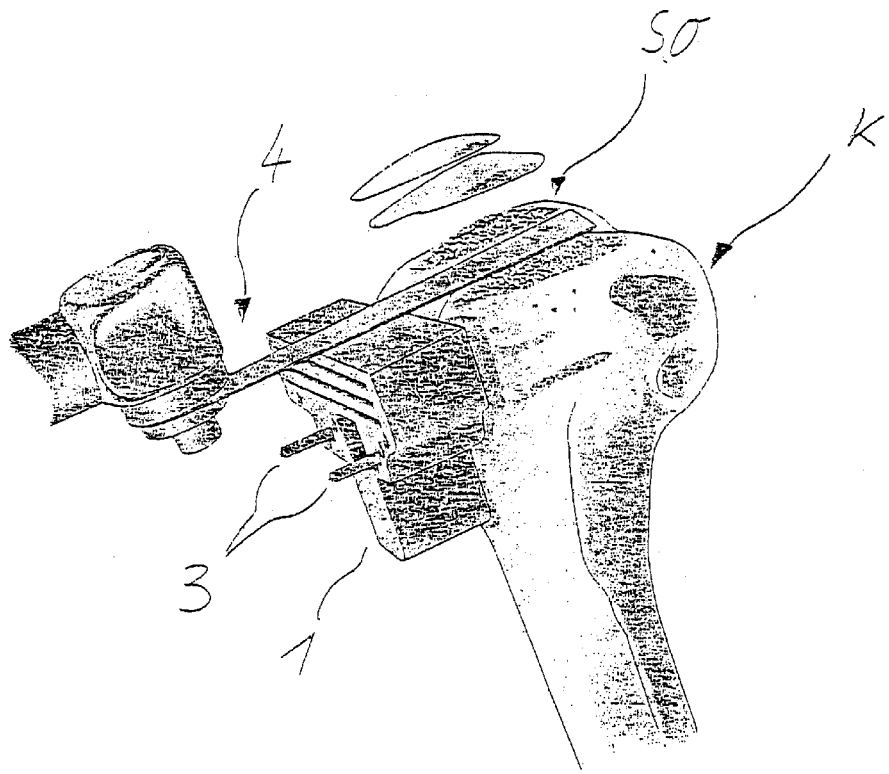
FIGS. 4A and 4B the incision of a bone using a first incision block positioned in accordance with the first embodiment.

FIG. 1 shows a first embodiment of the device 20 in accordance with the invention, comprising a reference star 21 and spherical elements 22a to 22c with reflecting surfaces, arranged on it. Two infrared cameras (not shown) detect light reflected on the spherical elements 22a to 22c, which are also designated as markers, and from this, the spatial location of the reference star 21 can be determined. The reference star 21 is firmly connected to a base body 22, on which a rotatable element 23 is arranged. The axial direction of the rotating element in the embodiment shown cannot be changed in its fixed orientation to the reference star 21. Two plates 24a, 24b of different thicknesses are arranged at the external end of the rotatable element 23 in such a way that the plates 24a, 24b lie in a plane and the vertical on the respective plate planes is parallel to the plane of rotation of the rotatable element 23. One of these plates 24a, 24b can be inserted into a guide slot 1a of the tibial incision block shown in FIGS. 2A to 2E, or into one of the guide slots II, III of the femoral incision block shown in FIG. 3. In this way, creating the incision in a first incision plane S0 as shown in FIG. 4 only requires navigating the incision block 1 with respect to the desired incision plane, i.e. navigating relative to the guide slit 1a. For this, the guide slit 1a can be shifted into the desired incision plane, as the cutting device 4 guided by the incision block 1 only has to be guided in the desired incision plane S0.

FIG. 3 shows a femoral incision block, wherein a cutting instrument may be guided either through the bearing surface I shown in FIG. 3 top, or through one of the two guide slits II or III.

Figure 4B:
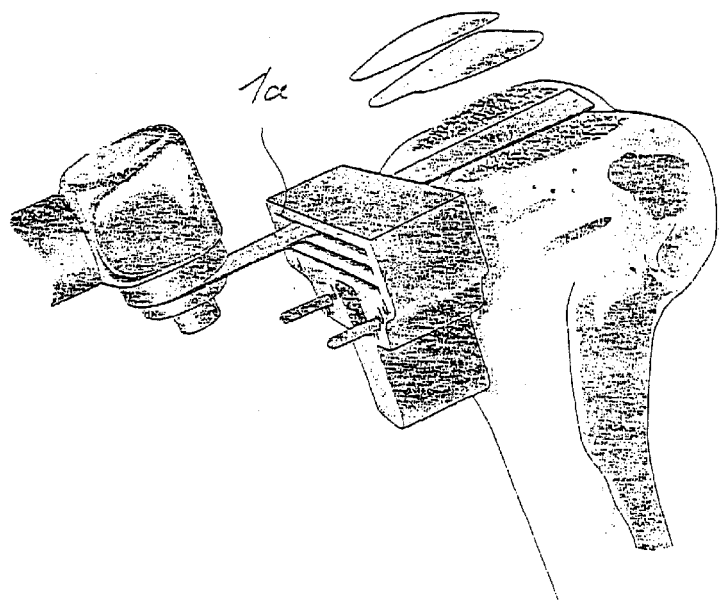

If, for example, the tibial incision block 1 shown in FIG. 2 is navigated onto a bone K using the positioning element 20 inserted into the guide slit 1a, as shown in FIG. 1, then this incision block 1 can be fixed to the bone K with suitable fixing or holding elements 3, as shown in FIG. 4. Using a cutting tool 4, a desired incision in the incision plane S0 can be made either by placing a blade on the upper side of the incision block 1, or by guiding a blade in a guide slit 1a, as shown in FIG. 4B.

The second embodiment of the invention for determining the position of an incision block, as shown in FIGS. 5A and 5B, comprises a reference star 31 such as in the first embodiment shown in FIG. 1, wherein only the holding elements 33a to 33c for attaching spherical elements with reflecting surfaces are shown in FIGS. 5A and 5B. A drill template 34 comprising two drill holes 35a, 35b is firmly connected to the reference star 31. Spikes 37 may be provided on the underside of the template 34 shown in FIG. 5B, to temporarily hold the template 34 in place. The drill template shown in FIG. 5 can by positioned by the reference star 31 on the incision plane S0 shown in FIG. 4 in such a way that suitable tools for creating a connecting structure between the bone and the incision block, for example holding elements 36, are inserted through the holes 35a and 35b into the bone K, such that the second incision block 10, as shown in diagram form in FIG. 6, can be correctly positioned by attaching it to the holding element(s) 36. In the same way, a holding element 36 can for example also be firmly connected to the incision block 10 in such a way that the incision block 10 can be inserted into the holes, drilled into the bone K with the aid of the drill template 34, using the holding element 36. Once the second incision block 10 has been placed in the desired position, the desired incisions in the planes S1 to S4 may be made, through the various guide slits provided in the second incision block 10.

An artificial joint can be attached onto a bone, in which the desired incision planes S0 to S4 have been created with the help of the first incision block 1 and the second incision block 10, said joint being correctly positioned when the location of the incision planes S0 to S4 is correct.

FIG. 7A shows a first device 40 in accordance with the invention, with which a reference star 41 with mountings 42a to 42c arranged on it may be attached to a bone or other structure, for attaching reflecting markers (not shown) in a defined positional relationship. The reference star 41, fixed for example to a bone, serves as a reference system for navigating and positioning the devices shown in FIG. 1 and FIG. 5. The device shown in FIG. 7 can, however, also be used independently of the elements and devices described above.

The spikes 43 shown on the underside of the device 40, which are connected to the shell 45, can be driven in or out by turning the screw 44. If, for example, a rod, such as for example a Schantz screw or a Kirschner wire is inserted into a bone, in order to attach the device 40, then the device 40 can be firmly attached to this rod fixed in the bone using the shell 45. The screw 46 serves to fix the device 40 to this rod. Once it has successfully been fixed in place by means of the screw 46, the nut 44 can be turned in order to move the spikes 43 downward, to thus effect a tensing of the device 40 with respect to the bone or another element, such as for example skin, or elements attached to the skin. A stable and non-shiftable connection between a reference star 41 and only a single rod in a bone can thus be obtained, since tightening via the spikes 43 which can be driven in or out is possible. The position of the reference star 41 can be changed by means of the screws 47 and 48 by turning about two axes.

Figure 7B:
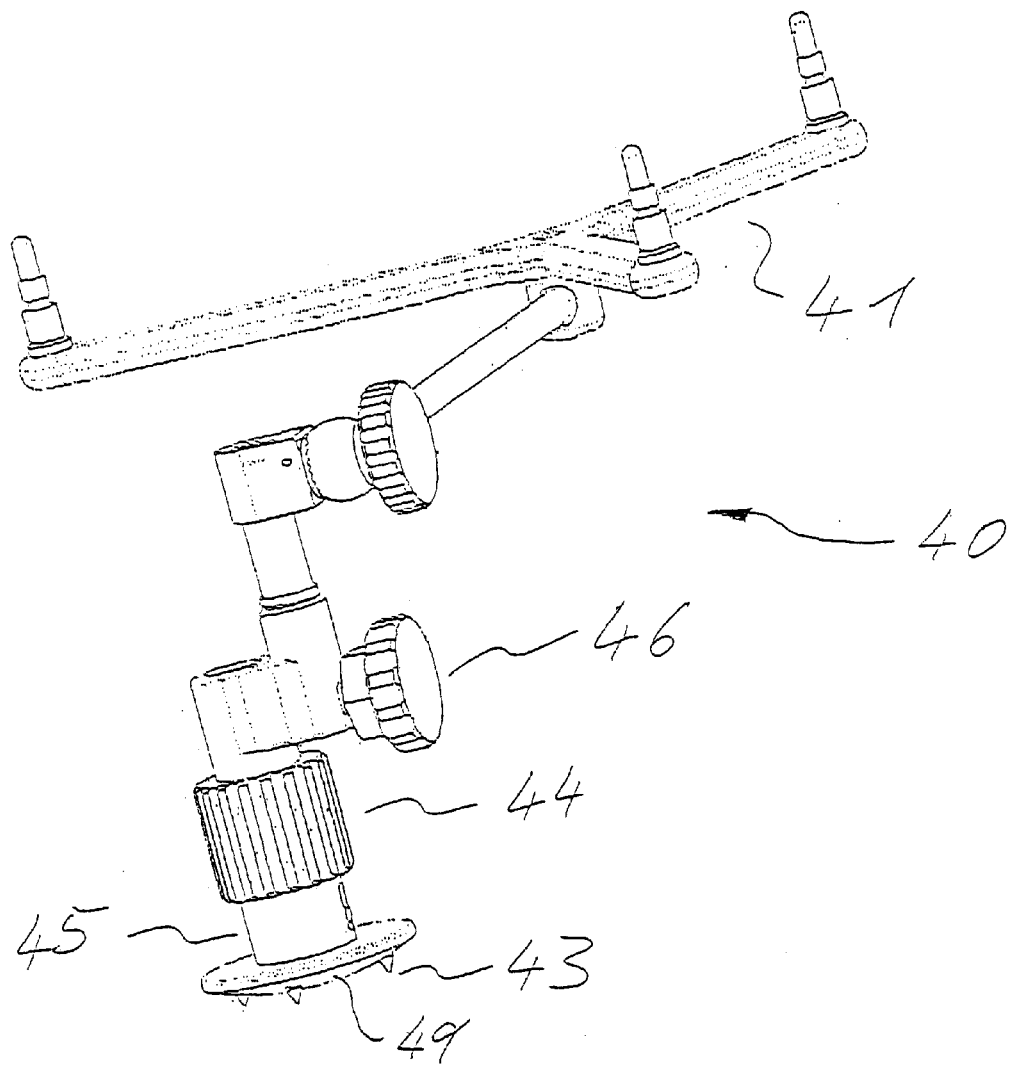

FIG. 7B shows a second embodiment of a device 40 for attaching a stable reference star 41, wherein the spikes 43 are arranged on a supporting surface 49, and are moved downward with the surface 49 in order to so tense the device 40 firmly against the skin surface.

Although the invention has been described in particular with respect to knee implants, it can of course also be used for other implants or procedures. In particular, the device for navigating the incision block, the device for navigating the hole template, and the clamping device shown in FIG. 7 can be used in this way, independently of one another.

What is claimed is:

1. A device for determining the position of an incision block, comprising:
   a positioning element, with at least one reference point, whose spatial position can be detected; and
   a position determining element, which is firmly connected to said positioning element;
   wherein said position determining element is a hole template for preparing and/or creating a connecting structure; and said hole template comprises at least two holes.

2. A system for positioning an incision block, comprising:
   a device for determining the position of an incision block, including:
      a positioning element, with at least one reference point, whose spatial position can be detected; and
      a position determining element, which is firmly connected to said positioning element; and
   an incision block and/or a position determining element, said position determining element being a hole template for preparing and/or creating a connecting structure.

3. The system as set forth in claim 2, comprising a device for attaching a positioning element to a bone in a stable manner.

4. A positioning device for positioning an incision block comprising:
   a positioning element having at least one detectable reference element that can be detected by a navigation device; and
   a position determining element connected to the positioning element, the position determining element being configured to interact with the incision block such that movement of the incision block with reference to the positioning determining element is restricted along at least one axis.

5. The positioning device of claim 4, wherein the at least one detectable reference elements is selected from the group consisting of active elements and passive elements.

6. The positioning device of claim 4, wherein the positioning element comprises a reference star having at least three detectable reference elements.

7. The positioning device of claim 4, wherein the position determining element is rotatable with respect to the positioning element.

8. The positioning device of claim 4, wherein the position determining element comprises at least one plate configured for insertion into a guide slit of the incision block.

9. The positioning device of claim 4, wherein the plate resides in a plane fixed in relation to the positioning element, and the plate can be rotated and/or shifted within said plane.

10. The positioning device of claim 4, wherein the position determining element comprises at least two plates differing in at least one of thickness and diameter.

11. A system for positioning incisions made to a bone, comprising an incision block; and the positioning device of claim 4.

12. A method for positioning an incision block comprising the steps of:
- causing the positioning device of claim 4 to interact with the incision block; and
- positioning the incision block by detecting the location of the at least one detectable reference element of the positioning device.

13. The method of claim 12, wherein the positioning device interacts with the incision block such that movement of the incision block with reference to the positioning device is restricted to a plane perpendicular to said axis.

14. The method of claim 12, further comprising the step of securing the incision block to a bone.

15. A positioning device for positioning a connecting element into a bone comprising:
- a positioning element having at least one detectable reference element that can be detected by a navigation device; and
- a template connected to the positioning element for use in placing at least one connecting element into a bone, the template including at least one of a guide hole and guide slot.

16. The positioning device of claim 15, wherein the template includes spikes for holding the template in position relative to the bone.

* * * * *